United States Patent
Zhang et al.

(10) Patent No.: US 9,462,983 B2
(45) Date of Patent: Oct. 11, 2016

(54) APPARATUS AND METHOD TO CONTROL MOVEMENT OF PHOTON-COUNTING DETECTORS IN A COMPUTED-TOMOGRAPHY (CT) SCANNER

(71) Applicant: Toshiba Medical Systems Corporation, Otawara-shi (JP)

(72) Inventors: Yuexing Zhang, Naperville, IL (US); Xiaolan Wang, Buffalo Grove, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 36 days.

(21) Appl. No.: 14/603,030

(22) Filed: Jan. 22, 2015

(65) Prior Publication Data
US 2016/0213339 A1    Jul. 28, 2016

(51) Int. Cl.
*A61B 6/03* (2006.01)
*H05G 1/30* (2006.01)
*H05G 1/60* (2006.01)
*H05G 1/64* (2006.01)
*A61B 6/00* (2006.01)

(52) U.S. Cl.
CPC ............ *A61B 6/4452* (2013.01); *A61B 6/032* (2013.01); *A61B 6/482* (2013.01); *A61B 6/488* (2013.01)

(58) Field of Classification Search
USPC ............. 250/370.09; 378/4, 8, 9, 12, 19, 21, 378/24–27, 210, 901
See application file for complete search history.

(56) References Cited

U.S. PATENT DOCUMENTS

| | | | |
|---|---|---|---|
| 7,136,452 B2 * | 11/2006 | Spartiotis | A61B 6/14 250/370.09 |
| 2013/0251097 A1 | 9/2013 | Zou | |
| 2014/0270056 A1 * | 9/2014 | Zou | A61B 6/4266 378/19 |
| 2014/0341333 A1 * | 11/2014 | Wang | A61B 6/032 378/19 |
| 2015/0146844 A1 | 5/2015 | Zamyatin et al. | |

OTHER PUBLICATIONS

U.S. Appl. No. 14/499,939, filed Sep. 29, 2014, Gagnon, et al.

\* cited by examiner

*Primary Examiner* — Bernard Souw
(74) *Attorney, Agent, or Firm* — Oblon, McClelland, Maier & Neustadt, L.L.P.

(57) ABSTRACT

A computed-tomography (CT) apparatus that includes a CT scanner including an X-ray source, a plurality of photon-counting detectors (PCDs) arranged in a fixed detector ring to capture incident X-ray photons emitted from the X-ray source, and control circuitry configured to move at least one PCD of the plurality of PCDs, from a first position to a second position, in response to receiving an instruction to perform a scanogram scan of an object.

19 Claims, 11 Drawing Sheets

APPARATUS AND METHOD TO CONTROL MOVEMENT OF PHOTON-COUNTING DETECTORS IN A COMPUTED-TOMOGRAPHY (CT) SCANNER

FIELD

Embodiments described herein relate to controlling movement of photon-counting detectors (PCDs) in a computed-tomography (CT) scanner.

BACKGROUND

A scanogram or scout image is a preliminary image obtained prior to performing scan data acquisition. During scanogram scans, PCDs in CT scanners create shadows on the X-ray detector. These shadows severely degrade the scanogram images resulting from the scan.

BRIEF DESCRIPTION OF THE DRAWINGS

The disclosure will be better understood from reading the description which follows and from examining the accompanying figures. These figures are provided solely as non-limiting examples of the embodiments. In the drawings.

DETAILED DESCRIPTION

In one embodiment, a CT apparatus includes a CT scanner including an X-ray source; a plurality of PCDs arranged in a fixed detector ring to capture incident X-ray photons emitted from the X-ray source; and control circuitry configured to move at least one PCD of the plurality of PCDs, from a first position to a second position, in response to receiving an instruction to perform a scanogram scan of an object.

In one embodiment, a CT apparatus includes a CT scanner including an X-ray source; a plurality of PCDs arranged in a fixed detector ring to capture incident X-ray photons emitted from the X-ray source; and control circuitry configured to tilt the detector ring from a first position to a second position, in response to receiving an instruction to perform a scanogram scan of an object.

In one embodiment, a method for a CT apparatus includes moving at least one PCD of a plurality of PCDs from a first position to a second position, in response to receiving an instruction to perform a scanogram scan of an object, the plurality of PCDs being arranged in a fixed detector ring to capture incident X-ray photons emitted from an X-ray source included in a CT scanner of the CT apparatus.

In one embodiment, a CT apparatus includes a CT scanner including an X-ray source; a plurality of photon-counting detectors (PCDs) arranged in a fixed detector ring to capture incident X-ray photons emitted from the X-ray source, each PCD including a first crystal and a second crystal, wherein a first PCD of the plurality of PCDs is located at a predetermined position on the detector ring and includes a gap between the first crystal and the second crystal to allow an X-ray beam projected from the X-ray source to pass therethrough, the first PCD being located on the X-ray source side between an object and the X-ray source.

Figure 1:
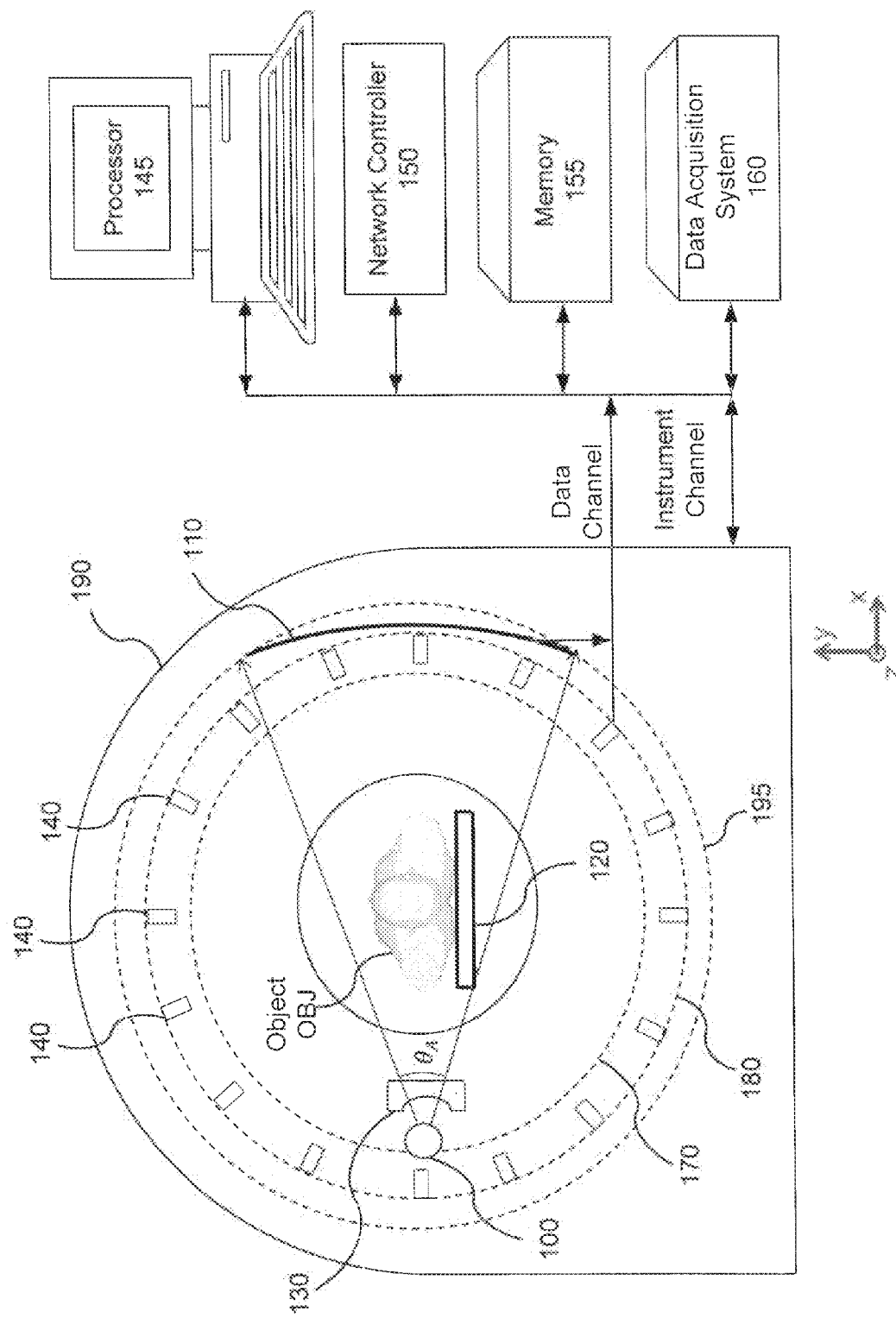
FIG. 1 illustrates a CT scanning system.
Figure 2:
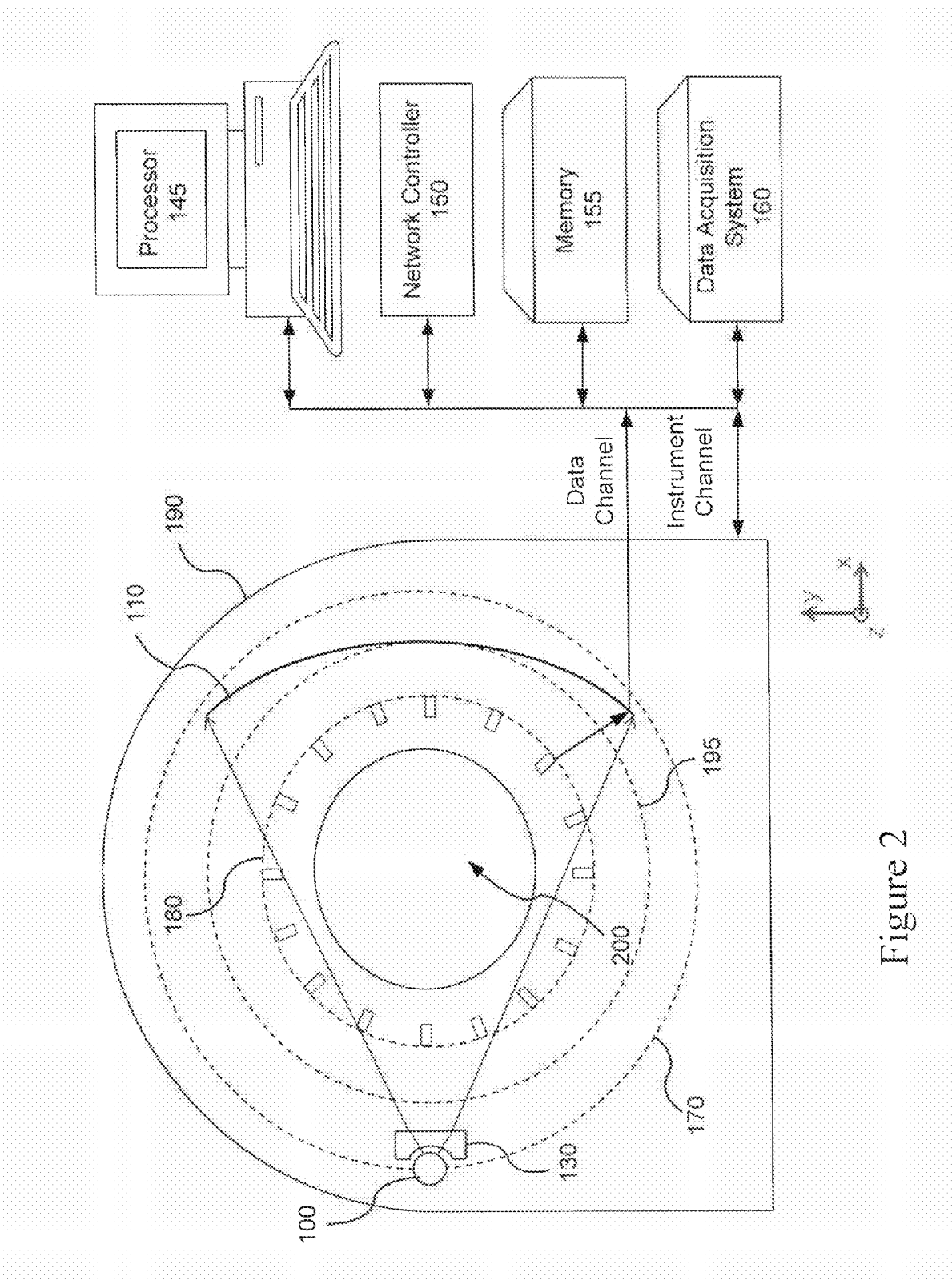
FIG. 2 illustrates a CT scanning system.

FIGS. 1 and 2 show schematic views of CT scanner systems with hybrid systems having energy-integrating detectors arranged in a third-generation geometry and PCDs arranged in a fourth-generation geometry. FIG. 1 shows a coupled-ring topology with the X-ray source 100 inside the ring of PCDs and the X-ray detector 110 outside the ring of PCDs, as discussed in U.S. patent application Ser. No. 13/426,903, incorporated herein by reference in its entirety. In contrast, FIG. 2 shows an inner-ring topology with both the X-ray source 100 and the X-ray detector 110 outside the ring of PCDs, as discussed in U.S. patent application Ser. No. 14/092,998, incorporated herein by reference in its entirety.

Illustrated in FIG. 1 is an implementation for placing the PCDs 140 in a predetermined fourth-generation geometry in combination with the X-ray detector 110 in a predetermined third-generation geometry in a CT scanner system. The diagram illustrates relative positions among an object OBJ to be scanned resting on a table 120, the X-ray source 100, a collimator/filter 130, the X-ray detector 110, and the PCDs 140. The PCDs 140 have a front surface, oriented towards the object OBJ and a back surface oriented away from the object OBJ. X-rays traveling through the object OBJ are either detected by the PCDs 140 (at the front surface) or pass through the spaces between the sparsely arranged PCDs 140 and are detected by the tightly packed energy-integrating detectors in the X-ray detector 110.

Also shown in FIG. 1 is circuitry and hardware for acquiring, storing, processing, and distributing X-ray projection data. The circuitry and hardware include: a processor (e.g., CPU) 145, a network controller 150, a memory 155, and a data acquisition system 160. In one implementation, the X-ray source 100 and the collimator/filter 130 are fixedly connected to a rotational component 170 that is rotatably connected to a gantry 190. The X-ray detector 110 is similarly fixedly connected to a rotational component 195 that is rotatably connected to the gantry 190. The PCDs 140 are fixedly connected to a circular component 180 that is fixedly connected to the gantry 190. The gantry 190 houses many pieces of the CT scanner.

The gantry of the CT scanner also includes an open aperture 200 (shown in FIG. 2) enabling the object OBJ that is arranged on a table 120 positioned in a projection plane of the X-rays traveling from the X-ray source to the PCDs 140 and the detector 110. The "projection plane" is a volume wherein X-rays pass from the X-ray source 100 to the detectors including the PCDs 140 and the detector 110. The "object space" is the intersection of the projection plane and the open aperture 200 of the gantry. The "image space" includes the union of projection planes corresponding to all projection angles of the X-ray source 100, as the X-ray source rotates around the aperture of the gantry. The image space is generally larger than the object space enabling image reconstruction for a volume extending beyond the dimension of the object OBJ.

A scan is performed when an object OBJ occupies the object space and the X-ray source is rotated through a series of projection angles with the CT scanner acquiring projection data of the X-ray transmission/attenuation through the object OBJ at each projection angle.

In general, the PCDs 140 each output a photon count for each of a predetermined number of energy bins. In addition to the PCDs 140 arranged in the fourth-generation geometry, the implementation shown in FIG. 1 includes the detector 110 having energy-integrating detectors arranged in a conventional third-generation geometry. The detector elements in the detector 110 can be more densely placed along the detector surface than the photon-counting detectors.

In one implementation, the PCDs are sparsely placed around the object OBJ in a predetermined geometry such as a circle. For example, the PCDs 140 are fixedly placed on a predetermined second circular component 180 in a gantry. In one implementation, the PCDs 140 are fixedly placed on the circular component 180 at predetermined equidistant positions. In an alternative implementation, the PCDs 140 are fixedly placed on the circular component 180 at predetermined non-equidistant positions. The circular component 180 remains stationary with respect to the object OBJ and does not rotate during the data acquisition.

Both the X-ray source 100, collimator 130 (e.g., a bow-tie filter), and the detector 110 rotate around the object OBJ while the PCDs 140 are stationary with respect to the object OBJ. In one implementation, the X-ray source 100 projects X-ray radiation with a predetermined source fan beam angle $\theta_A$ towards the object OBJ while the X-ray source 100 rotates around the object OBJ outside the sparsely placed PCDs 140. Furthermore, the detector 110 is mounted at a diametrically opposed position from the X-ray source 100 across the object OBJ and rotates outside the stationary circular component 180, on which the PCDs 140 are fixed in a predetermined sparse arrangement.

In one implementation, the X-ray source 100 optionally travels a helical path relative to the object OBJ, wherein the table 120 moves the object OBJ linearly in a predetermined direction perpendicular to the rotational plane of the rotating portion 170 as the rotating portion 170 rotates the X-ray source 100 and the detector 110 in the rotational plane.

The motion of the rotating portion 170 around the object OBJ is controlled by a motion control system. The motion control system can be integrated with a data acquisition system or can be separate providing one way information regarding the angular position of the rotating portion 170 and the linear position of the table 120. The motion control system can include position encoders and feedback to control the position of the rotating portion 170 and the table 120. The motion control system can be an open loop system, a closed loop system, or a combination of an open loop system and a closed loop system. The motion control system can use linear and rotary encoders to provide feedback related to the position of the rotating portion 170 and the position of the table 120. The motion control system can use actuators to drive the motion of the rotating portion 170 and the motion of the table 120. These positioners and actuators can include: stepper motors, DC motors, worm drives, belt drives, and other actuators known in the art.

The CT scanner also includes a data channel that routes projection measurement results from the PCDs 140 and the detector 110 to the data acquisition system 160, the processor 145, the memory 155, and the network controller 150. In one embodiment, the data acquisition system 160 has a similar configuration as the computer system 1201 illustrated in FIG. 11. The data acquisition system 160 controls the acquisition, digitization, and routing of projection data from the detectors. The data acquisition system 160 also includes radiography control circuitry to control the rotation of the annular rotating frames 170 and 195. In one implementation data acquisition system 160 will also control the movement of the bed 120, the operation of the X-ray source 100, and the operation of the X-ray detectors 110. The data acquisition system 160 can be a centralized system or alternatively it can be a distributed system. In an implementation, the data acquisition system 160 is integrated with the processor 145. The processor 145 performs functions including reconstructing images from the projection data, pre-reconstruction processing of the projection data, and post-reconstruction processing of the image data.

The pre-reconstruction processing of the projection data can include correcting for detector calibrations, detector nonlinearities, polar effects, noise balancing, and material decomposition. Post-reconstruction processing can include filtering and smoothing the image, volume rendering processing, and image difference processing as needed. The image reconstruction process can be performed using filtered back-projection, iterative image reconstruction methods, or stochastic image reconstruction methods. Both the processor 145 and the data acquisition system 160 can make use of the memory 155 to store, e.g., projection data, reconstructed images, calibration data and parameters, and computer programs.

The processor 145 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art. The memory 155 can be a hard disk drive, CD-ROM drive, DVD drive, FLASH drive, RAM, ROM or any other electronic storage known in the art.

The network controller 150, such as an Intel Ethernet PRO network interface card from Intel Corporation of America, can interface between the various parts of the CT scanner. Additionally, the network controller 150 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In one implementation, the X-ray source 100 is optionally a single source. In another implementation, the X-ray source 100 is configured to perform a kV-switching function for emitting X-ray radiation at a predetermined high-level energy and at a predetermined low-level energy. In still another alternative embodiment, the X-ray source 100 is a single source emitting a broad spectrum of X-ray energies. In still another embodiment, the X-ray source 100 includes multiple X-ray emitters with each emitter being spatially and spectrally distinct.

The detector 110 can use energy-integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline (e.g., NaI(Tl), CsI (Tl), CsI(Na), CsI(pure), CsF, KI(Tl), LiI(Eu), $BaF_2$, $CaF_2$ (Eu), ZnS(Ag), $CaWO_4$, $CdWO_4$, YAG(Ce), $Y_3Al_5O_{12}$(Ce), GSO, LSO, $LaCl_3$(Ce), $LaBr_3$(Ce), LYSO, BGO, $LaCl_3$ (Ce), $LaBr_3$(Ce), $C_{14}H_{10}$, $C_{14}H_{12}$, and $C_{10}H_8$), an organic liquid (e.g., an organic solvent with a flour such as p-terphenyl ($C_{18}H_{14}$), PBD ($C_{20}H_{14}N_2O$), butyl PBD ($C_{24}H_{22}N_2O$), or PPO ($C_{15}H_{11}NO$)), a plastic (e.g., a flour suspended in a solid polymer matrix), or other know scintillator.

The PCDs 140 can use a direct-conversion X-ray radiation detectors based on semiconductors, such as cadmium telluride (CdTe), cadmium zinc telluride (CZT), silicon (Si), mercuric iodide ($HgI_2$), and gallium arsenide (GaAs). Semiconductor based direct-conversion X-ray detectors generally have much faster time response than indirect-conversion detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

FIG. 2 illustrates an inner ring topology for a CT scanner. The primary difference between the CT scanner in FIG. 1 and the CT scanner in FIG. 2 is that in FIG. 2 the X-ray source 100 and the rotational component 170 to which the X-ray source 100 is fixed are outside the circular component 180 to which the PCDs 140 are fixed. In one implementation, the back surface of each PCD 140 is provided a protective rear cover to shield the PCDs 140 from irradiation from behind as the X-ray source 100 travels outside the first circular component 180 of the sparsely placed photon-counting detectors.

Both the X-ray source 100, collimator 130 (e.g., a bow-tie filter), and the detector 110 rotate around the object OBJ in aperture 200 while the PCDs 140 are stationary with respect to the object OBJ in aperture 200. In one implementation, the X-ray source 100 and collimator 130 are mounted on the first rotation component 170 mounted in the gantry 190 so that the X-ray source 100 projects X-ray radiation with a predetermined source fan beam angle $\theta_A$ towards the object OBJ while the X-ray source 100 rotates around the object OBJ outside the sparsely placed PCDs 140. Furthermore, the detector 110 having energy-integrating detectors arranged in a third-generation geometry is mounted on the second rotation component 195 that is rotatably fixed to the gantry 190. The detector 110 is maintained at a position diametrically opposed from the X-ray source 100 with the object OBJ in the intermediary space between the X-ray source 100 and the detector 110—the rotation components 170 and 195 rotating outside the stationary circular component 180, on which the PCDs 140 are fixed in a predetermined sparse arrangement.

As discussed above, a scanogram or scout image is a preliminary projection image obtained prior to performing scan data acquisition. Scanogram images do not require high image quality and are used to roughly estimate dimensions and/or compositions of a patient to aid the prescription of CT protocols. In particular, scanogram images may be used to ensure the region of interest is included in the field of view or to check the exposure technique.

In the above-discussed configurations shown in FIGS. 1 and 2, the PCDs 140 create shadows on the detector 110 during scanogram scans. For the inner ring configuration shown in FIG. 2, the PCDs 140 at the X-ray source 100 side cause large shadows that severely degrade the scanogram images.

Figure 3:
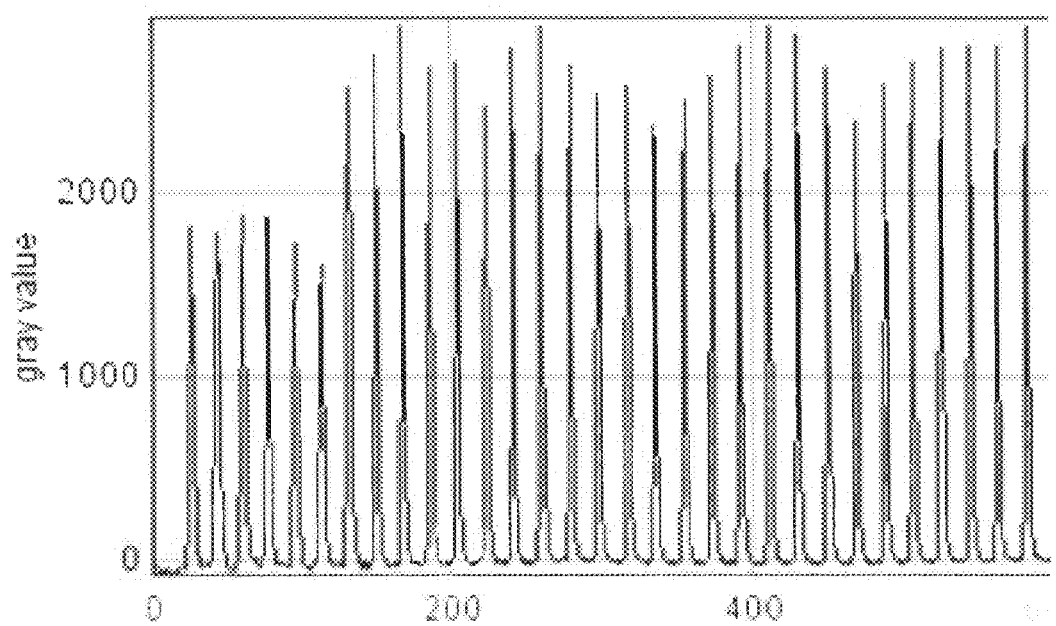
FIG. 3 illustrates a graph that depicts shadows on a detector.
Figure 4:
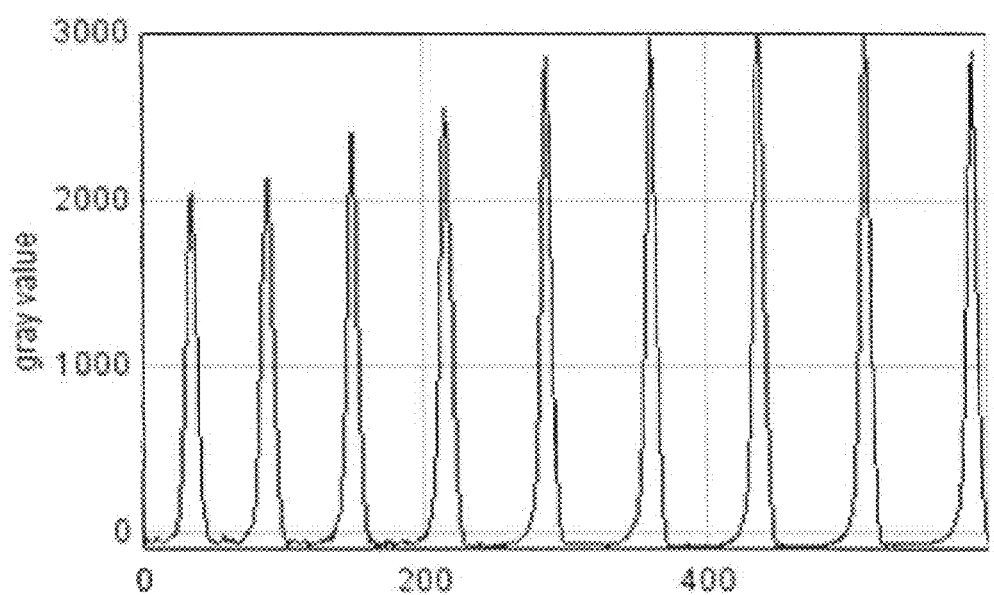
FIG. 4 illustrates a graph that depicts shadows on a detector.

FIG. 3 illustrates a graph that depicts shadows on the detector 110 when the PCDs 140 are at the detector 110 side (configuration of FIG. 1). FIG. 4 illustrates a graph that depicts shadows on the detector 110 when the PCDs 140 are at the X-ray source 100 side (configuration of FIG. 2).

In one embodiment, in order to minimize or eliminate shadows in the configuration of FIG. 2, the PCDs 140 at the X-ray source 100 side are physically moved out of the X-ray beam path. In particular, the PCDs 140 at the X-ray source 100 are moved outside the X-ray beam path before the scanogram scan, and then moved back to their original position after the scanogram scan and before scan data acquisition.

In one embodiment, the aforementioned PCDs 140 at the X-ray source 100 that are moved can be defined as the PCDs within the predetermined source fan beam angle $\theta_A$. In one embodiment, additional PCDs (not necessarily included within the predetermined source fan beam angle $\theta_A$) may also be moved.

Figure 5:
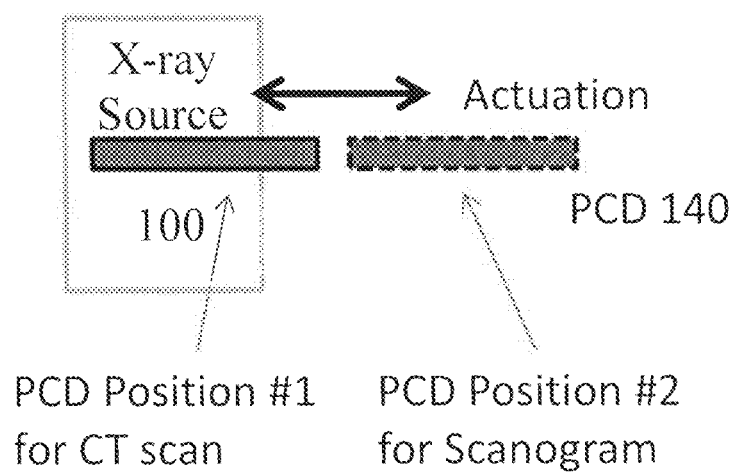
FIG. 5 illustrates movement of a PCD.

FIG. 5 illustrates how each PCD 140 can be moved outside the X-ray beam path before the scanogram scan, according to one embodiment. As can be seen in FIG. 5, each PCD is moved laterally (from side to side) such that PCD position #2 is parallel to the initial PCD position #1.

Figure 6:
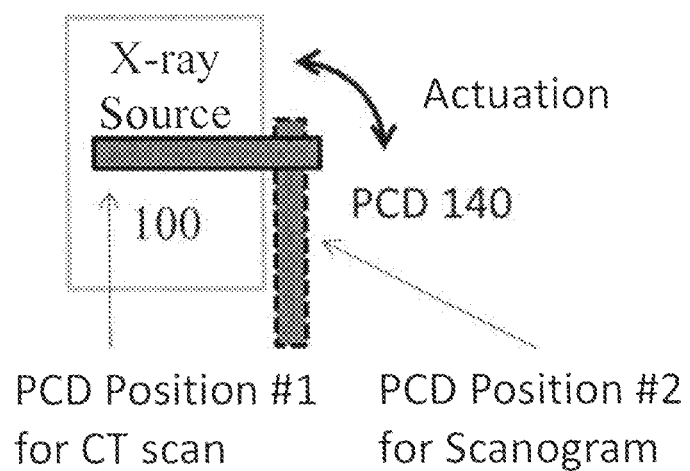
FIG. 6 illustrates movement of a PCD.

FIG. 6 illustrates how each PCD 140 can be moved outside the X-ray beam path before the scanogram scan, according to one embodiment. As can be seen in FIG. 6, each PCD is moved such that PCD position #2 is perpendicular to the initial PCD position #1.

Note that both of the aforementioned figures represent views from the iso-center toward the X-ray source 100 (i.e., along the x direction in FIGS. 1 and 2). Thus, the PCDs 140 are moved in the z direction in FIG. 5 and rotated in the y-z plane about the x-axis in FIG. 6.

Figure 7:
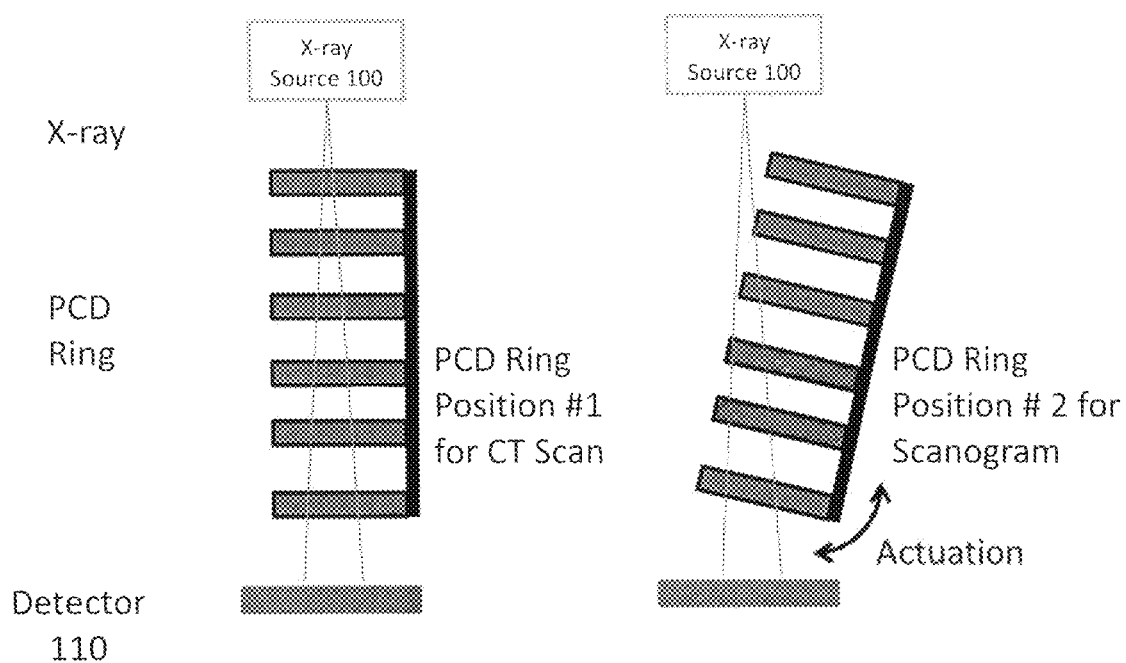
FIG. 7 illustrates tilting of a detector ring.

FIG. 7 illustrates how the entire detector ring can be tilted during the scanogram scan in order to move the PCDs 140 at the X-ray source 100 outside the X-ray beam path, according to one embodiment. Note that FIG. 7 represents a side view, and the PCD ring is tilted in the z direction (i.e., into the page in FIGS. 1 and 2).

Note that the distance a PCD is moved may not be the same for all PCDs, and is predetermined based on the geometry of the scanner. In one embodiment, the distance may be calculated based on the mechanical design and moving pattern (e.g., parallel move out, tilt, etc.). For example, in the parallel move shown in FIG. 5, the distance is such that PCDs are fully retracted from the beam path. In the tilt design shown in FIG. 7, the distance is such that the PCDs near the X-ray source are fully retracted from the beam path.

Figure 8:
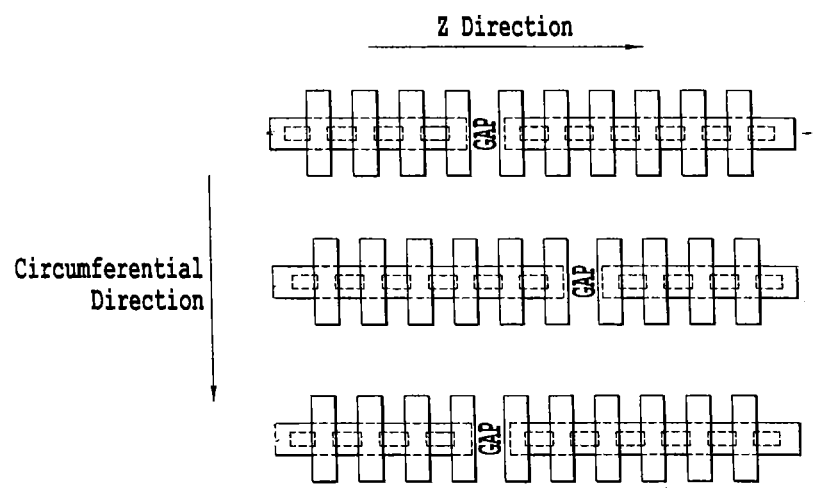
FIG. 8 illustrates an arrangement in which longer and shorter PCDs along the z-axis are alternated circumferentially around the detector ring.

As discussed in U.S. patent application Ser. No. 14/499, 939, incorporated herein by reference in its entirety, FIG. 8 illustrates a configuration in which longer and shorter monolithic crystals arranged in the z direction are alternated circumferentially around the detector ring so that the "seam" between crystals (i.e., the gap illustrated in FIG. 8) does not always appear in the same transaxial plane. Note that the gaps are arranged as shown in FIG. 8 in a normal state. However, in scanogram scans, the gaps are arranged so as to align with each other.

As discussed in U.S. patent application Ser. No. 14/499, 939, the gaps between consecutive crystals in PCDs are at alternating z locations around the ring. Such arrangement applies to "wide-cone" multi-slice scans in which more than one pixelated detector sensor is needed to achieve large z coverage.

Figure 9:
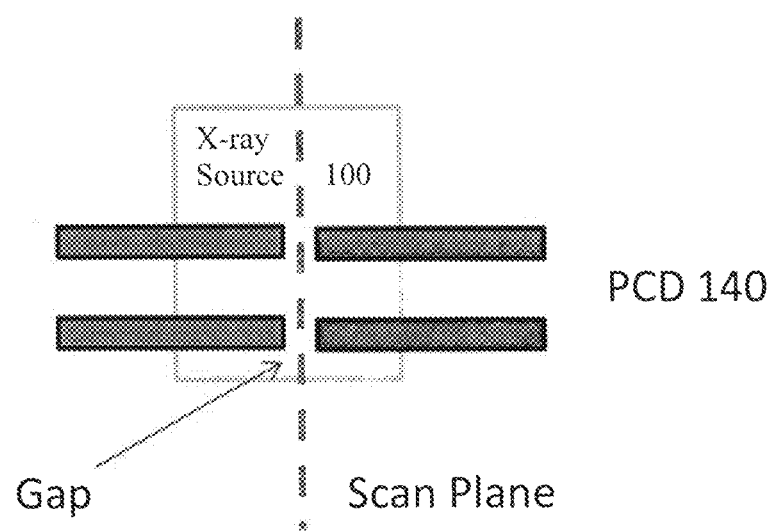
FIG. 9 illustrates a gap placed between PCDs.

In one embodiment, the gap can be placed between crystals of PCDs 140 at the X-ray source 100 side for scanogram scans. This configuration is illustrated in FIG. 9. X-ray source 100 positions for scanogram scans are typically at one or more predetermined positions (i.e., 12 o'clock, 3 o'clock, 6 o'clock, and/or 9 o'clock). Note that, aside from the aforementioned positions, the gap can be somewhere else at other angular positions around the ring.

Note that, typically a human body can be approximated by an ellipse. Thus, in one embodiment, the projection angles are top-down (12 o'clock/6 o'clock) and left-right (9 o'clock/3 o'clock), as the CT scanner needs to capture the ellipse along the long and short axis for scan prescription (right FOV, bowtie, mA, kVp, etc.) and other correction/ calibration purposes.

In this embodiment, the gap is placed such that the X-ray beam can pass without obstruction during the scanogram scan (in light of the aforementioned positions). Further, in one embodiment, the gap is only placed between crystals of PCDs 140 at the X-ray source 100 side (included within the predetermined source fan beam angle $\theta_A$), and the opposing side of PCDs 140 at the detector 110 side does not have such gaps.

In one embodiment, the placement of the gap is permanent. In other words, in such an embodiment, the location of the gap does not change based on whether a scanogram is being performed. As a scanogram utilizes a few pre-selected projection angles (for example, one along 12 o'clock/6 o'clock and one along 9 o'clock/3 o'clock), the gap can be permanently placed among these few positions without jeopardizing scan quality.

The movement of the PCDs 140 and the ring of the PCDs discussed above are controlled by one or more apparatuses or systems. For example, in one embodiment, the movement of the PCDs 140 and ring can be controlled by the motion control system and/or the data acquisition system 160, and/or another system/apparatus. These systems/apparatuses can use one or more controllers to control one or more actuators/motors, as discussed above.

Furthermore, in one embodiment, such systems can control each PCD on the ring independently. In one embodiment, such systems can control groups of two or more PCDs independently from other groups of PCDs. In one embodiment, such systems can control some PCDs individually and others as a group. Such features provide maximum flexibility by being able to control one or more PCDs at a time.

Figure 10:
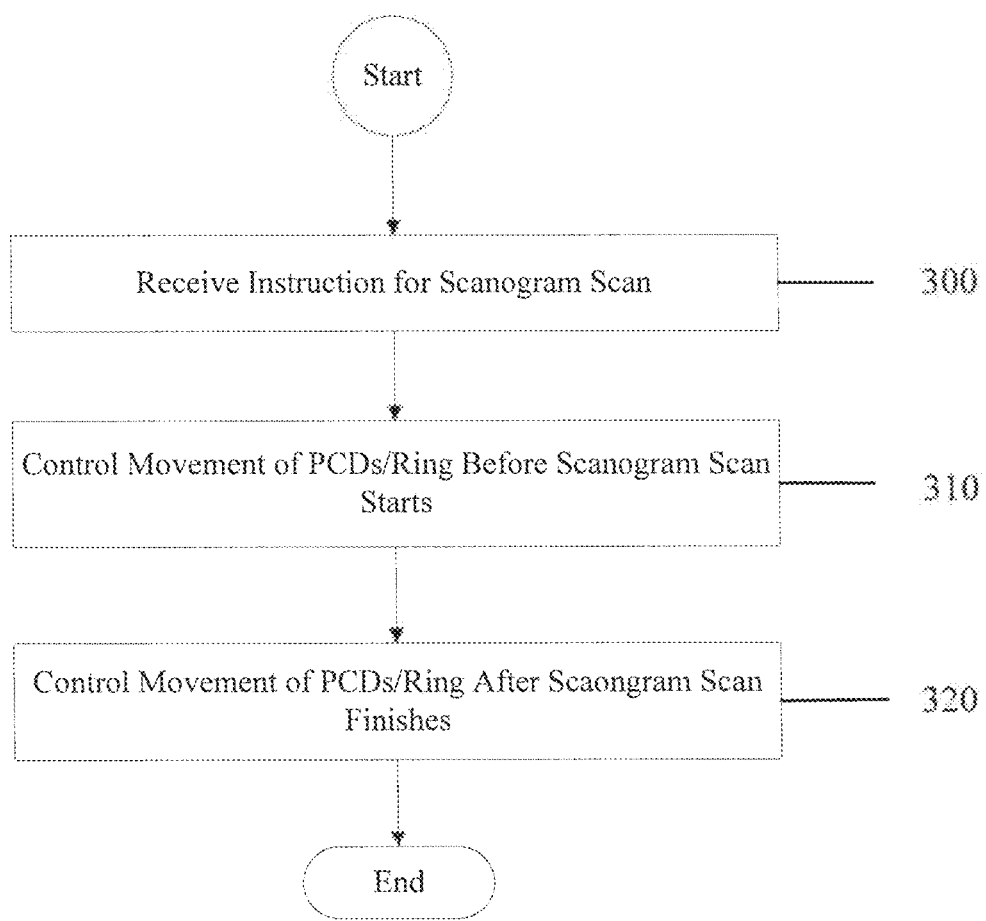
FIG. 10 illustrates a flowchart of a process according to one embodiment.

FIG. 10 illustrates a flowchart of a process performed by control circuitry of an apparatus/system, according to one embodiment. The apparatus/system has a similar configuration as the computer system 1201 illustrated in FIG. 11. At step 300, the apparatus receives an instruction to perform a scanogram scan.

At step 310, the apparatus controls movement of the PCDs or detector ring (as discussed above) before the scanogram scan starts, in response to receiving the instruction to perform a scanogram scan. Thus, at step 310, the PCDs or detector ring is moved from a first initial position to a second position so as to be outside the X-ray beam path.

Next, at step 320, the apparatus controls movement of the PCDs or detector ring after the scanogram scan finishes. Thus, at step 320, the PCDs or detector ring is moved from the second position back to the first initial position.

Each of the functions of the described embodiments may be implemented by the control circuitry, which includes one or more processing circuits. A processing circuit includes a programmed processor (for example, processor 145 or 1203), as a processor includes circuitry. A processing circuit also includes devices such as an application specific integrated circuit (ASIC) and conventional circuit components arranged to perform the recited functions.

Figure 11:
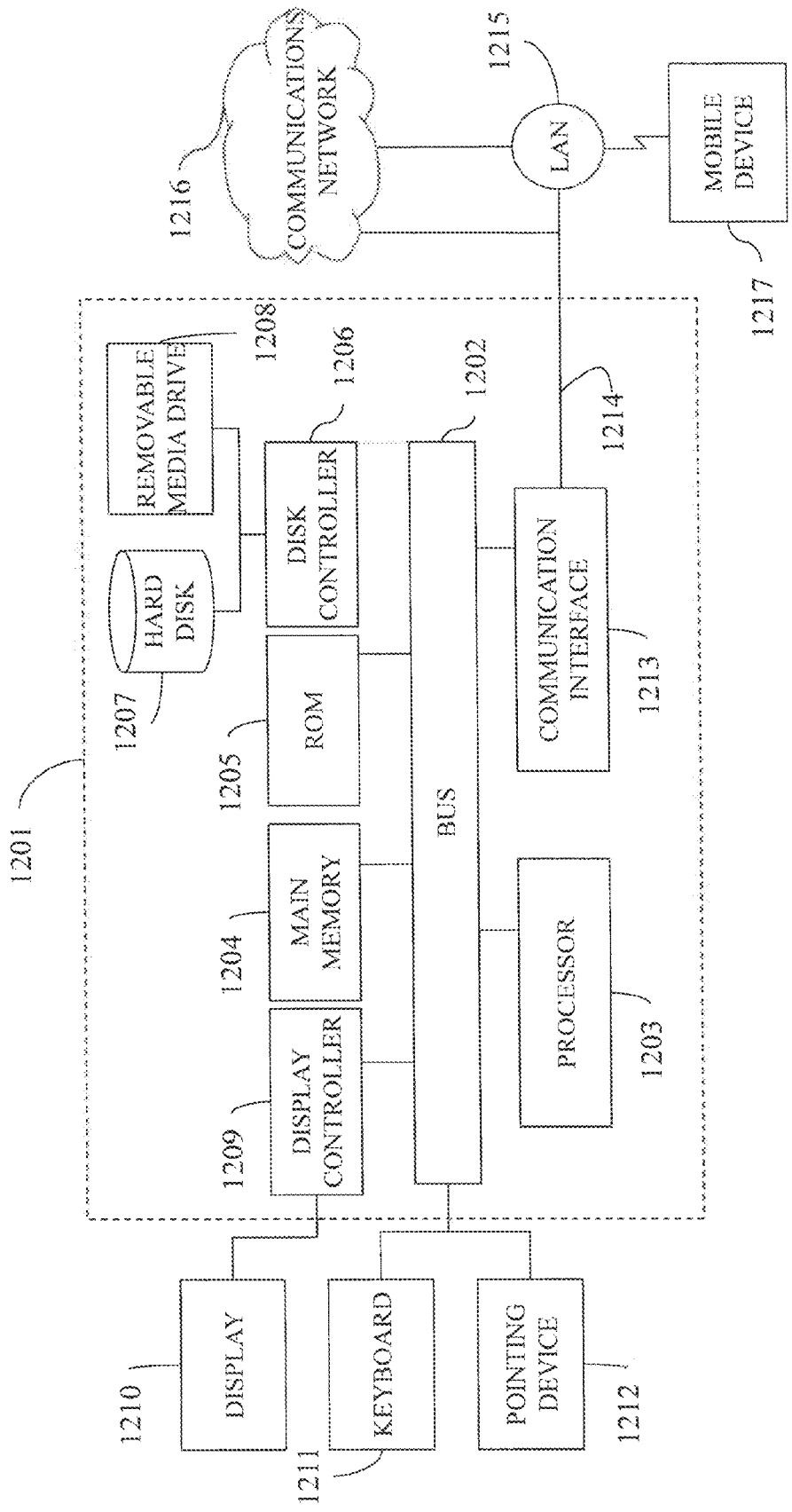
FIG. 11 illustrates a computer system upon which features of a CT apparatus may be implemented.

The various features discussed above may be implemented by a computer system (or programmable logic). FIG. 11 illustrates such a computer system 1201. The computer system 1201 includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, for displaying information to a computer user. The computer system includes input devices, such as a keyboard 1211 and a pointing device 1212, for interacting with a computer user and providing information to the processor 1203. The pointing device 1212, for example, may be a mouse, a trackball, a finger for a touch screen sensor, or a pointing stick for communicating direction information and command selections to the processor 1203 and for controlling cursor movement on the display 1210.

The processor 1203 executes one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to any of the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present disclosure includes software for controlling the computer system 1201, for driving a device or devices for implementing the invention, and for enabling the computer system 1201 to interact with a human user. Such software may include, but is not limited to, device drivers, operating systems, and applications software. Such computer readable media further includes the computer program product of the present disclosure for performing all or a portion (if processing is distributed) of the processing performed in implementing any portion of the invention.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1203 for execution. A computer readable medium may take many forms, including but not limited to, non-volatile media or volatile media. Non-volatile media includes, for example, optical, magnetic disks, and magneto-optical disks, such as the hard disk 1207 or the removable media drive 1208. Volatile media includes dynamic memory, such as the main memory 1204. Transmission media, on the contrary, includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 1201 may receive the data on the telephone line and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an integrated services digital network (ISDN) card. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc.). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214 and the communication interface 1213. Moreover, the network link 1214 may provide a connection through a LAN 1215 to a mobile device 1217 such as a personal digital assistant (PDA) laptop computer, or cellular telephone.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A computed-tomography (CT) apparatus, comprising:
a CT scanner including an X-ray source;
a plurality of photon-counting detectors (PCDs) arranged in a fixed detector ring to capture incident X-ray photons emitted from the X-ray source; and
control circuitry configured to move at least one PCD of the plurality of PCDs, from a first position to a second position, in response to receiving an instruction to perform a scanogram scan of an object.

2. The CT apparatus of claim 1, wherein the control circuitry is further configured to move the at least one PCD from the second position back to the first position after the scanogram scan has been performed.

3. The CT apparatus of claim 1, wherein the at least one PCD that is moved is located on the X-ray source side between the object and the X-ray source.

4. The CT apparatus of claim 3, wherein, at the first position, the at least one PCD is within a path of an X-ray beam projected from the X-ray source.

5. The CT apparatus of claim 4, wherein, at the second position, the at least one PCD is outside the path of the X-ray beam projected from the X-ray source.

6. The CT apparatus of claim 1, wherein the control circuitry is configured to move the at least one PCD from the first position to the second position in a z direction, which is along a length of the object.

7. The CT apparatus of claim 1, wherein the control circuitry is configured to move the at least one PCD from the first position to the second position in a y-z plane about the x-axis, which is along a width of the object.

8. A computed-tomography (CT) apparatus, comprising:
a CT scanner including an X-ray source;
a plurality of photon-counting detectors (PCDs) arranged in a fixed detector ring to capture incident X-ray photons emitted from the X-ray source; and
control circuitry configured to tilt the detector ring from a first position to a second position, in response to receiving an instruction to perform a scanogram scan of an object.

9. The CT apparatus of claim 8, wherein the control circuitry is further configured to tilt the detector ring from the second position back to the first position after the scanogram scan has been performed.

10. The CT apparatus of claim 8, wherein the control circuitry is further configured to tilt the detector ring from the first position to the second position such that a subset of the plurality of PCDs are outside a path of an X-ray beam projected from the X-ray source.

11. The CT apparatus of claim 10, wherein the subset of PCDs are located on the X-ray source side between the object and the X-ray source.

12. A method for a computed-tomography (CT) apparatus, the method comprising:
moving at least one photon-counting detector (PCD) of a plurality of PCDs from a first position to a second position, in response to receiving an instruction to perform a scanogram scan of an object, the plurality of PCDs being arranged in a fixed detector ring to capture incident X-ray photons emitted from an X-ray source included in a CT scanner of the CT apparatus.

13. The method of claim 12, wherein the moving moves the at least one PCD from the second position back to the first position after the scanogram scan has been performed.

14. The method of claim 12, wherein the at least one PCD that is moved is located on the X-ray source side between the object and the X-ray source.

15. The method of claim 14, wherein, at the first position, the at least one PCD is within a path of an X-ray beam projected from the X-ray source.

16. The method of claim 15, wherein, at the second position, the at least one PCD is outside the path of the X-ray beam projected from the X-ray source.

17. A computed-tomography (CT) apparatus, comprising:
a CT scanner including an X-ray source;
a plurality of photon-counting detectors (PCDs) arranged in a fixed detector ring to capture incident X-ray photons emitted from the X-ray source, each PCD including a first crystal and a second crystal, wherein
a first PCD of the plurality of PCDs is located at a predetermined position on the detector ring and includes a gap between the first crystal and the second crystal to allow an X-ray beam projected from the X-ray source to pass therethrough, the first PCD being located on the X-ray source side between an object and the X-ray source.

18. The CT apparatus of claim 17, wherein
the predetermined position of the first PCD corresponds to one of four positions located 90 degrees apart from each other.

19. The CT apparatus of claim 18, wherein
a second PCD of the plurality of PCDs is located at another of the four positions and includes the gap between the first crystal and the second crystal.

\* \* \* \* \*